United States Patent
Toguchi et al.

(10) Patent No.: US 6,948,353 B2
(45) Date of Patent: Sep. 27, 2005

(54) QUICK RESPONSE STRUCTURE OF GAS SENSOR

(75) Inventors: Kengo Toguchi, Aichi-ken (JP); Makoto Mashida, Oobu (JP); Kazuhiro Okazaki, Aichi-ken (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/202,825

(22) Filed: Jul. 26, 2002

(65) Prior Publication Data

US 2003/0019280 A1 Jan. 30, 2003

(30) Foreign Application Priority Data

Jul. 27, 2001 (JP) ........................................ 2001-228203
Jun. 5, 2002 (JP) ........................................ 2002-164769

(51) Int. Cl.[7] ................................................ G01N 7/00
(52) U.S. Cl. ........................ 73/23.31; 73/31.05; 204/424
(58) Field of Search .............................. 73/23.31, 23.32, 73/31.05; 204/424–429

(56) References Cited

U.S. PATENT DOCUMENTS

| 1,798,977 | A | * | 3/1931 | Erickson ........................ 422/99 |
| 4,328,295 | A | * | 5/1982 | Tanaka et al. ................. 429/304 |
| 4,507,192 | A |  | 3/1985 | Ebizawa |
| 5,238,552 | A |  | 8/1993 | Kato et al. |
| 5,609,825 | A | * | 3/1997 | Fukaya et al. ................. 422/90 |
| 6,202,469 | B1 | * | 3/2001 | Nakamura et al. ........... 73/23.31 |
| 6,214,186 | B1 | * | 4/2001 | Watanabe et al. ............ 204/428 |
| 6,254,926 | B1 | * | 7/2001 | Katafuchi et al. ........... 427/125 |
| 6,258,234 | B1 | * | 7/2001 | Watanabe et al. ............ 204/424 |
| 6,279,376 | B1 | * | 8/2001 | Yamada et al. ............... 73/23.2 |
| 6,327,891 | B1 | * | 12/2001 | Noda et al. ................. 73/31.05 |
| 6,346,179 | B1 | * | 2/2002 | Makino et al. .............. 204/428 |
| 2003/0121782 | A1 | * | 7/2003 | Atsumi et al. ............... 204/424 |

FOREIGN PATENT DOCUMENTS

| DE | 199 35 301 | 2/2000 |  |
| EP | 0 978 721 | 2/2000 |  |
| JP | 63298147 A | * 12/1988 | ................ 73/31.05 |
| JP | 2641346 | 5/1997 |  |
| JP | 2000-171429 | 6/2000 |  |

OTHER PUBLICATIONS

Patent Abstrac of Japan—vol. 1999, No. 12, Oct. 29, 1999 & JP 11 183428; Jul. 9, 1999.
Patent Abstracts of Japan—vol. 1999, No. 05, May 31, 1999 & JP 11 044669; Feb. 16, 1999.

* cited by examiner

*Primary Examiner*—Michael Cygan
(74) *Attorney, Agent, or Firm*—Nixon & Vanderhye PC

(57) ABSTRACT

A protective cover assembly of a gas sensor which is made up of an inner and an outer cover. The inner cover is disposed within the outer cover coaxially through a given clearance. The dimension of the clearance is defined within a range suitable for improving the response rate of the gas sensor while ensuring the effect of avoiding the damage such as cracks in a sensor element arising from wetting thereof with moisture contained in a measurement gas.

16 Claims, 12 Drawing Sheets

QUICK RESPONSE STRUCTURE OF GAS SENSOR

BACKGROUND OF THE INVENTION

1. Technical Field of the Invention

The present invention relates generally to a gas sensor which may be installed in an exhaust system of an internal combustion engine to determine the concentration of $O_2$, NOx, HC, or CO in exhaust emissions, and more particularly to an improved structure of such a type of gas sensor designed to ensure a quick response to a change in, for example, concentration of a gas to be measured without sacrificing the effect of avoiding breakage of a sensor element.

2. Background Art

Conventionally, gas sensors are used for burning control of internal combustion engines for automotive vehicles. As a typical example, a gas sensor is installed in an exhaust pipe of an automotive engine to measure the concentration of a specified gas contained in exhaust emissions of the engine. A gas sensor of this type consists essentially of a gas sensor element disposed within a hollow cylindrical housing, an air cover installed on a base portion of the housing, and a protective cover assembly installed on a tip portion of the housing. The protective cover assembly has a double-walled structure made up of an inner and an outer cylindrical cover. The inner cover is smaller in diameter than the outer cover and disposed inside the outer cover coaxially.

The protective cover assembly has formed in the inner and outer covers a plurality of gas inlets through which the exhaust emissions enter a gas chamber defined in the cover assembly. The sensor element measures the concentration of the specified gas such as oxygen in the exhaust emissions admitted into the gas chamber.

Accurate measurement of the concentration of the specified gas subject to change cyclically requires use of gas sensors designed to provide a quick response to such a change. Further, the gas sensor element is apt to be wetted with moisture contained in the exhaust emissions, and may be broken. In order to avoid this, it is required to minimize the quantity of water entering the gas chamber through the gas inlets of the inner and outer covers.

Increasing the response rate of the gas sensors requires increasing the size of the gas inlets of the inner and outer covers, but it results in ease of intrusion of the moisture into the gas chamber. This is objectionable in avoiding the wetting of the gas sensor.

Single-walled protective covers are also known which are designed to simplify the flow of gas into the gas chamber for improving the response rate of the gas sensor, but it causes the sensor element to get wet directly with the moisture, thus accelerating the breakage such as cracks in the sensor element.

SUMMARY OF THE INVENTION

It is therefore an object of the invention to provide an improved structure of a gas sensor designed to ensure a rapid response to a change in, for example, concentration of a gas to be measured and to avoid undesirable wetting of a sensor element leading to the breakage of the sensor element.

According to one aspect of the invention, there is provided a gas sensor which may be employed in measuring the concentration of a specified gas contained in exhaust emissions of an internal combustion engine of an automotive vehicle. The gas sensor comprises: (a) a hollow cylindrical housing; (b) a gas sensor element retained within the housing which has a sensing portion working to sense a specified gas; and (c) a cover assembly installed on an end of the housing to define a gas chamber in which the sensing portion of the sensing element is disposed and into which the specified gas is admitted. The cover assembly is made up of an inner and an outer hollow cylindrical cover which are different in diameter and have gas inlets through which the specified gas passes. The inner cover is disposed within the outer cover coaxially with each other with a given clearance therebetween which lies within a range of 0.2 mm to 0.6 mm In the preferred mode of the invention, each of the gas inlets of the inner and outer covers of the cover assembly has an area within a range of 0.2 $mm^2$ to 20 $mm^2$.

Each of the inner and outer covers has a bottom in which a hole is formed.

Each of the inner and outer covers has a rounded corner formed between the bottom and a side wall thereof.

The sensor element has an electrode. The gas inlet of the inner cover of the cover assembly faces the electrode for directing the specified gas into the electrode.

The distance between a tip of the sensing portion of the sensor element remote from the housing and the gas inlet of the inner cover of the cover assembly is within a range of 1.5 mm to 15 mm.

The distance between an end of the outer cover of the cover assembly remote from the housing and the gas inlet of the outer cover is within a range of 1.5 mm to 15 mm.

The clearance between the inner and outer covers preferably lies within a range of 0.2 mm to 0.55 mm According to the second aspect of the invention, there is provided a gas sensor which comprises: (a) a hollow cylindrical housing; (b) a gas sensor element retained within the housing which has a sensing portion working to sense a specified gas; and (c) a cover assembly installed on an end of the housing to define a gas chamber in which the sensing portion of the sensing element is disposed and into which the specified gas is admitted. The cover assembly is made up of an inner and an outer hollow cylindrical cover which are arranged coaxially, different in diameter, and have gas inlets through which the specified gas passes. If a circle having the same area as a cross sectional area of the outer cover is defined as S1, and a circle having the same area as a cross sectional area of the inner cover is defined as S2, a difference in radius between the circles S1 and S2 is defined within a range of 0.2 mm to 0.6 mm.

In the preferred mode of the invention, each of the gas inlets of the inner and outer covers of the cover assembly has an area within a range of 0.2 $mm^2$ to 20 $mm^2$.

Each of the inner and outer covers has a bottom in which a hole is formed.

Each of the inner and outer covers has a rounded corner formed between the bottom and a side wall thereof.

The sensor element has an electrode. The gas inlet of the inner cover of the cover assembly faces the electrode in order to direct the specified gas to the electrode.

The distance between a tip of the sensing portion of the sensor element remote from the housing and the gas inlet of the inner cover of the cover assembly is within a range of 1.5 mm to 15 mm.

The distance between an end of the outer cover of the cover assembly remote from the housing and the gas inlet of the outer cover is within a range of 1.5 mm to 15 mm.

The difference in radius between the circles S1 and S2 lies preferably within a range of 0.2 mm to 0.55 mm.

According to the third aspect of the invention, there is provided a gas sensor which comprises: (a) a hollow cylindrical housing; (b) a gas sensor element retained within the housing which has a sensing portion working to sense a specified gas; and (c) a cover assembly installed on an end of the housing, the cover assembly being made up of an inner and an outer hollow cylindrical cover which are arranged coaxially and different in diameter. The cover assembly defines therein a gas chamber in which the sensing portion of the sensing element is disposed and into which a specified gas is admitted through gas inlets formed in the outer and inner covers. The volume of the gas chamber is defined within a range of 800 mm$^3$ to 1600 mm$^3$.

In the preferred mode of the invention, if the volume of the gas chamber is defined as V1, and a volume of a clearance defined between the inner and outer covers of the cover assembly is defined as V2, a relation of V2/V1≦0.25 is met.

Each of e gas inlets of the inner and outer covers of the cover assembly has an area within a range of 0.2 mm$^2$ to 20 mm$^2$.

Each of the inner and outer covers has a bottom in which a hole is formed.

Each of the inner and outer covers has rounded corner formed between the bottom and a side wall thereof.

The sensor element has an electrode. The gas inlet of the inner cover of the cover assembly faces the electrode in order to direct the specified gas to the electrode.

The distance between a tip of the sensing portion of the sensor element remote from the housing and the gas inlet of the inner cover of the cover assembly is within a range of 1.5 mm to 15 mm.

The distance between an end of the outer cover of the cover assembly remote from the housing and the gas inlet of the outer cover is within a range of 1.5 mm to 15 mm.

According to the fourth aspect of the invention, there is provided a gas sensor which comprises: (a) a hollow cylindrical housing; (b) a gas sensor element retained within the housing which has a sensing portion working to sense a specified gas; and (c) a cover assembly installed on an end of the housing to define a gas chamber in which the sensing portion of the sensing element is disposed and into which the specified gas is admitted. The cover assembly is made up of an inner and an outer hollow cylindrical cover which are arranged coaxially, different in diameter, and have gas inlets through which the specified gas passes. Each of the gas inlets of the outer cover is defined by a portion of a peripheral side wall which is cut and bent outward.

In the preferred mode of the invention, each of the gas inlets of the inner cover is defined by a portion of a peripheral side wall which is cut and bent outward.

Each of the gas inlets of the inner and outer covers of the cover assembly has an area within a range of 0.2 mm$^2$ to 20 mm$^2$.

Each of the inner and outer covers has a bottom in which a hole is formed.

Each of the inner and outer covers has a rounded corner formed between the bottom and a side wall thereof.

The sensor element has an electrode. The gas inlet of the inner cover of the cover assembly faces the electrode in order to direct the specified gas to the electrode.

The distance between a tip of the sensing portion of the sensor element remote from the housing and the gas inlet of the inner cover of the cover assembly is within a range of 1.5 mm to 15 mm.

The distance between an end of the outer cover of the cover assembly remote from the housing and the gas inlet of the outer cover is within a range of 1.5 mm to 15 mm.

According to the fifth aspect of the invention, there is provided a gas sensor which comprises: (a) a hollow cylindrical housing; (b) a gas sensor element retained within the housing which has a sensing portion working to sense a specified gas; and (c) a cover assembly installed on an end of the housing to define a gas chamber in which the sensing portion of the sensing element is disposed and into which the specified gas is admitted, the cover assembly being made up of an inner and an outer hollow cylindrical cover which are arranged coaxially, different in diameter, and have gas inlets through which the specified gas passes. The inner cover has a peripheral wall made up of a shoulder and a straight portion. The shoulder has a diameter increasing toward the end of the housing on which the cover assembly is installed and is located closer to the end of the housing than the gas inlets. The straight portion has a constant diameter.

In the preferred mode of the invention, the distance between one of ends of the shoulder remote from the housing and the gas inlet of the inner cover of the cover assembly is within a range of 0.2 mm to 2 mm.

The distance between one of ends of the shoulder remote from the housing and a bottom of the outer cover of the cover assembly is within a range of 1.5 mm to 15 mm.

Each of the gas inlets of the inner and outer covers of the cover assembly has an area within a range of 0.2 mm$^2$ to 20 mm$^2$.

Each of the inner and outer covers has a bottom in which a hole is formed.

Each of the inner and outer covers has a rounded corner formed between the bottom and a side wall thereof.

The sensor element has an electrode for picking up a sensor signal. The gas inlet of the inner cover of the cover assembly faces the electrode in order to direct the specified gas to the electrode.

The distance between a tip of the sensing portion of the sensor clement remote from the housing and the gas inlet of the inner cover of the cover assembly is within a range of 1.5 mm to 15 mm.

The distance between an end of the outer cover of the cover assembly remote from the housing and the gas inlet of the outer cover is within a range of 1.5 mm to 15 mm.

According to the sixth aspect of the invention, there is provided a gas sensor which comprises: (a) a hollow cylindrical housing; (b) a gas sensor element retained within the housing which has a sensing portion working to sense a specified gas; and (c) a cover assembly installed on an end of the housing to define a gas chamber in which the sensing portion of the sensing element is disposed and into which the specified gas is admitted, the cover assembly being made up of an inner and an outer hollow cylindrical cover which are arranged coaxially, different in diameter, and have gas inlets through which the specified gas passes. The inner cover is disposed within the outer cover coaxially with each other with a given clearance therebetween which has a volume lying within a range of 50 mm$^3$ to 200 mm$^3$.

In the preferred mode of the invention, if a volume of the gas chamber is defined as V1, and the volume of the clearance between the inner and outer covers of the cover assembly is defined as V2, a relation of V2/V1≦0.25 is met.

Each of the gas inlets of the inner and outer covers of the cover assembly has an area within a range of 0.2 mm$^2$ to 20 mm$^2$.

Each of the inner and outer covers has a bottom in which a hole is formed.

Each of the inner and outer covers has a rounded corner formed between the bottom and a side wall thereof.

The sensor element has an electrode for picking up a sensor output. The gas inlet of the inner cover of the cover assembly faces the electrode for direct the specified gas to the electrode.

The distance between a tip of the sensing portion of the sensor element remote from the housing and the gas inlet of the inner cover of the cover assembly is within a range of 1.5 mm to 15 mm.

The distance between an end of the outer cover of the cover assembly remote from the housing and the gas inlet of the outer cover is within a range of 1.5 mm to 15 mm.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
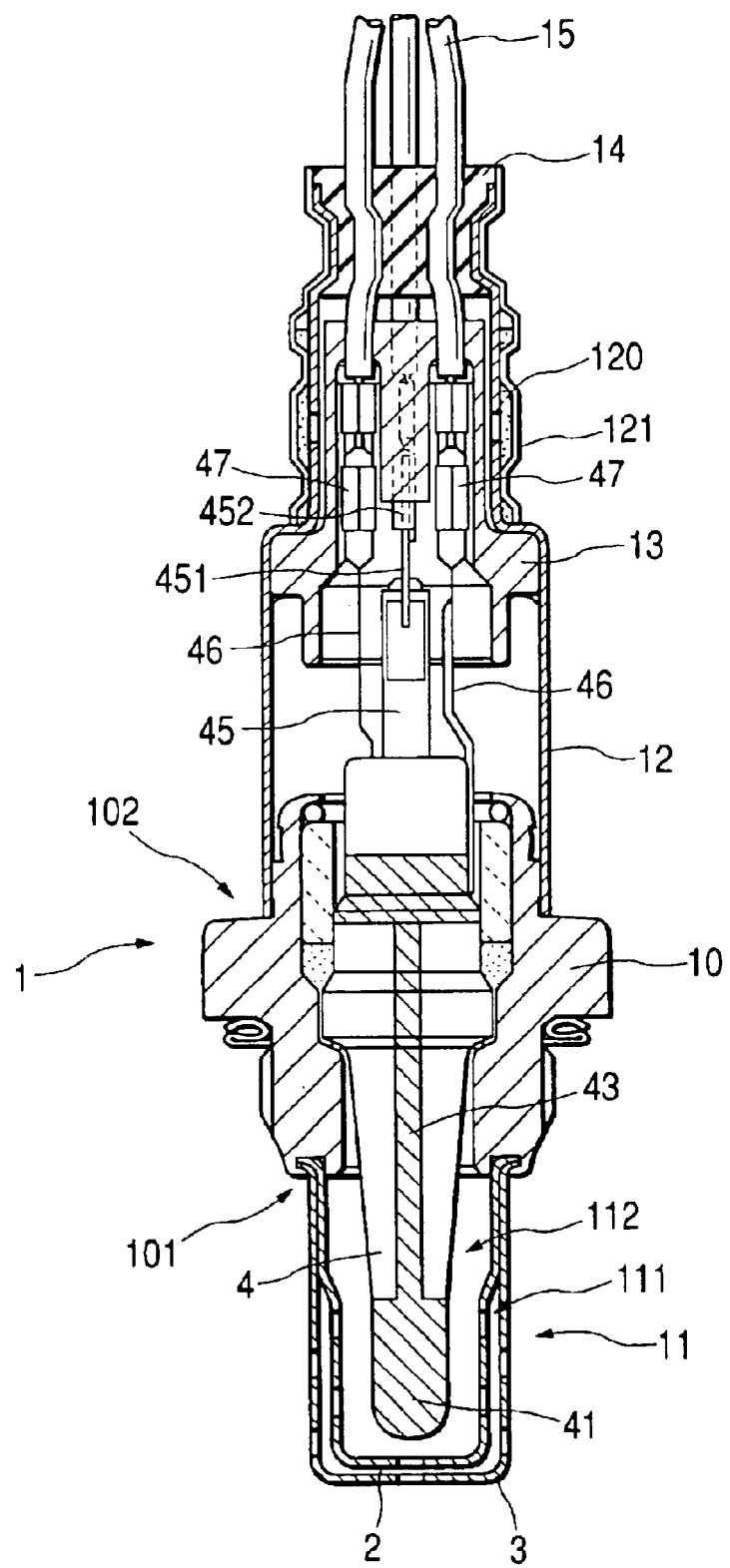
FIG. 1 is a longitudinal sectional view which shows a gas sensor equipped with a protective cover assembly according to the first embodiment of the invention.

Referring to the drawings, wherein like reference numbers refer to like parts in several views, particularly to FIG. 1, there is shown a gas sensor 1 according to the first embodiment of the invention which may be employed in a burning control system for automotive engines to measure the concentration of a gas component such as $O_2$, NOx, HC, or CO contained in exhaust gasses of the engine.

The gas sensor 1 generally includes a gas sensor element 4, a metallic hollow cylindrical housing 10, an air cover 12, and a protective cover assembly 11. The gas sensor element 4 is retained in the cylindrical housing 10 in a liquid tight fashion and has a head portion or sensing portion exposed outside the housing 10. The cover assembly 11 is attached to a head of the housing 10 and has a longitudinal center line 119, as shown in FIG. 3(a), extending in alignment with a longitudinal center line of the gas sensor 1 (i.e., the gas sensor element 4). The cover assembly 11 consists of a hollow cylindrical outer cover 3 and a hollow cylindrical inner cover 2 and has a flange (will also be referred to as a base below) installed in an annular groove formed in the end wall 101 of the housing 10 to define a gas chamber 112 within which the sensing portion of the gas sensor element 4 is disposed and into which a gas to be measured (will also be referred to as a measurement gas below) is admitted through gas inlets 241, 242, 341, and 342, as clearly shown in FIG. 2, formed in the outer and inner covers 2 and 3, respectively.

The inner cover 2 is smaller in diameter than the outer cover 3 and disposed inside the outer cover 3 coaxially. The inner cover 2 has a shoulder 23 to define a clearance 111 between an outer side wall of the inner cover 2 and an inner side wall of the outer cover 3. The clearance 111 is, as indicated by C in FIG. 3(a), defined within a range of 0.2 mm to 0.6 mm, and preferably within a range of 0.2 mm to 0.55 mm. The reason for setting the clearance 11 within such a range will be described later in detail.

Figure 4:
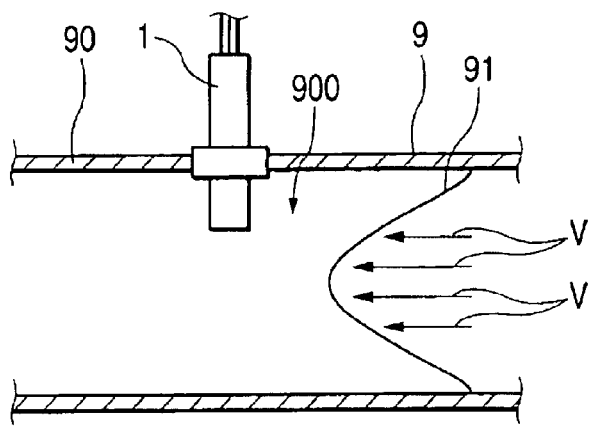
FIG. 4 is an illustration which shows a velocity profile of a gas flow passing through an exhaust pipe of an internal combustion engine.

The following discussion will refer to an example in which the gas sensor 1 is, as shown in FIG. 4, installed in a mount hole formed in a peripheral wall 90 of an exhaust pipe 9 of an automotive engine in contact of the housing 10 with the mount hole to measure the concentration of oxygen contained in exhaust emissions for use in the air-fuel ratio control.

Usually, an exhaust gas flow has a velocity profile 91, as shown in FIG. 4, within a flow passage 900 of the exhaust pipe 9. The velocity profile 91 is defined by illustrated velocity vectors V. Specifically, the velocity of a central stream of the gas flowing through the flow passage 900 is the greatest, and the velocity of a peripheral stream of the gas along an inner wall of the exhaust pipe 9 is the lowest.

Referring back to FIGS. 1 and 2, the air cover 12 is fitted on a boss of the housing 10. An outer cover 121 is provided around the air cover 12 and staked or crimped to retain a cylindrical water-repellent filter 120 on the periphery of the air cover 12. The air cover 12 and the outer cover 121 have formed therein air inlets through which air is admitted as a reference gas into an air chamber defined inside the air cover 12.

The cover assembly 11 has a double-walled structure made up of the inner and outer covers 2 and 3. The outer cover 3 has, as described above, the gas inlets 341 and 342 formed therein. Similarly, the inner cover 2 has the gas inlets 241 and 242 formed therein. The gas inlets 341, 342, 241, and 242 are of circular shape and identical in area with each other. In this embodiment, the area of each of the gas inlets 341, 342, 241, and 242 is 3.14 mm$^2$. The gas inlets 342, 342, 241, and 242 are all opposed to an outer electrode 41, as will be described later in detail, which is installed on the gas sensor element 4.

Figure 2:
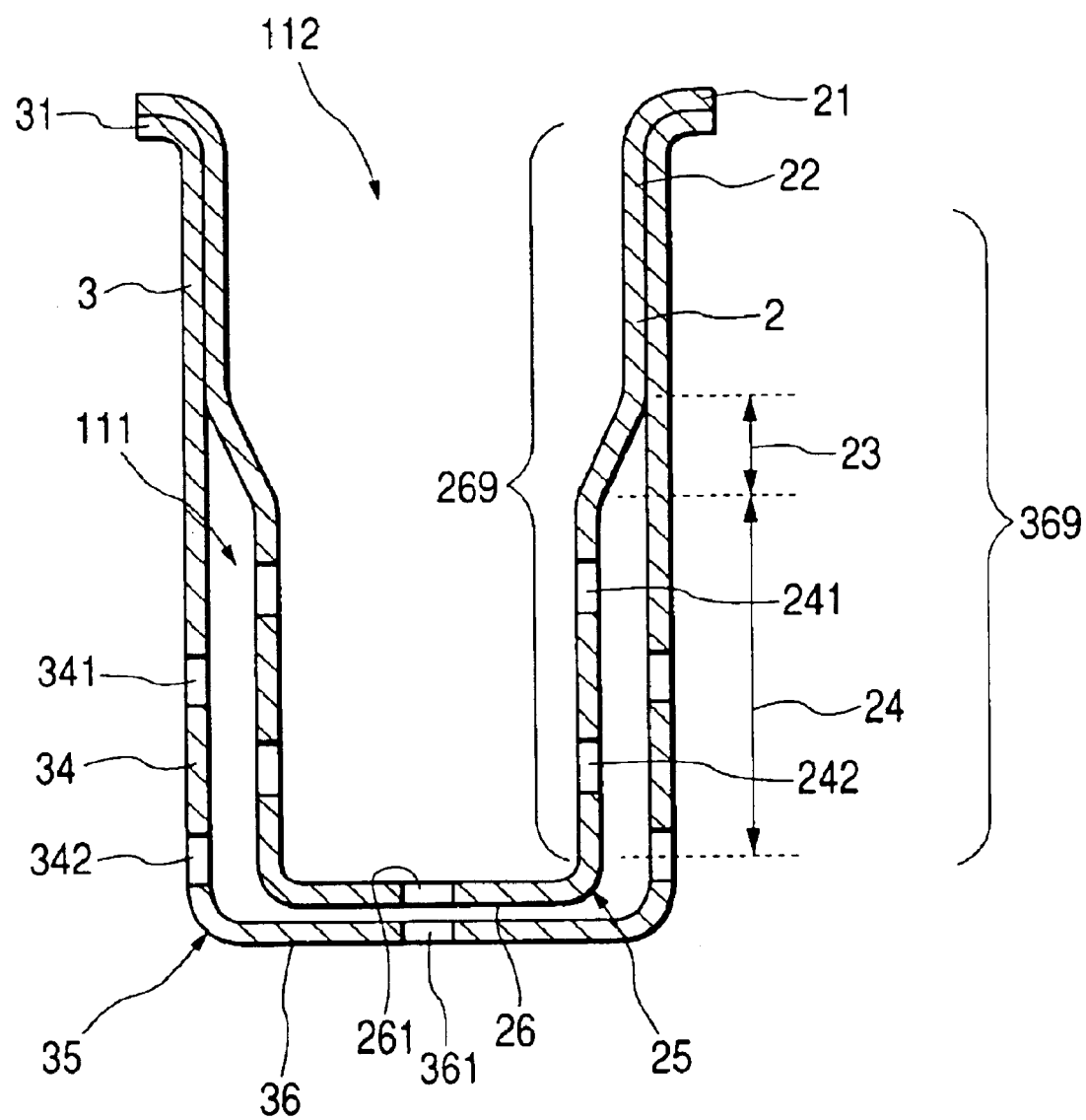
FIG. 2 is a sectional view which shows an internal structure of the protective cover assembly in FIG. 1.
Figure 3A:
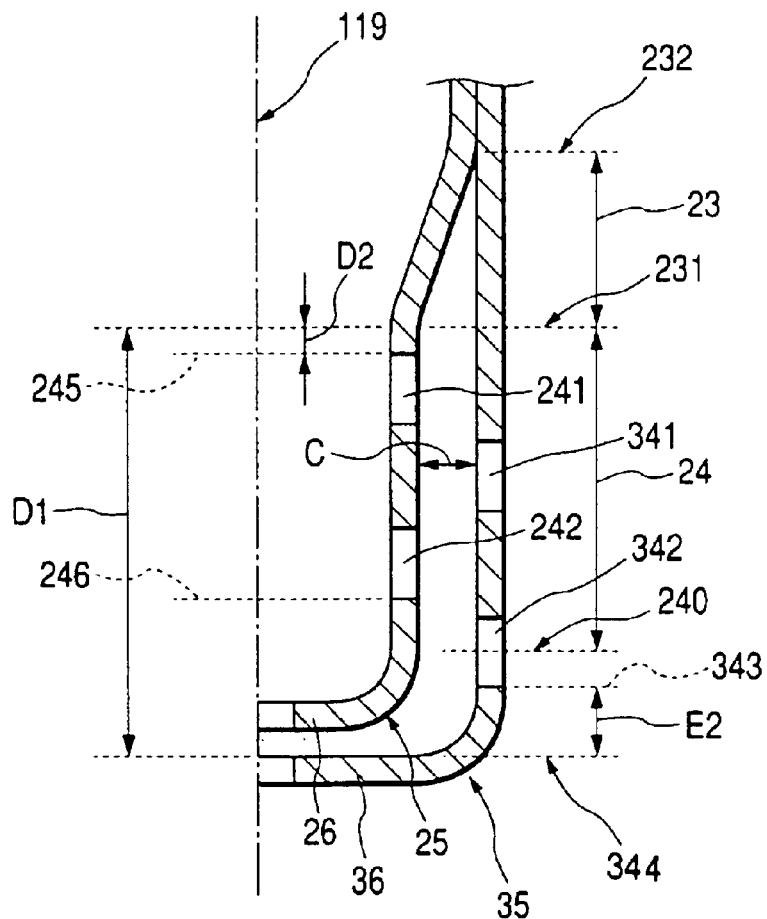
FIG. 3(a) is a partially enlarged view of FIG. 2.

The outer and inner covers 3 and 2 are, as clearly shown in FIG. 2, formed by hollow cylinders with bottoms 36 and 26. The bottoms 36 and 26 have circular holes 361 and 261. The outer and inner covers 3 and 2 have bottom corners 35 and 25 rounded between peripheries of the bottoms 335 and 25 and side walls 369 and 269, respectively.

The inner cover 2 is, as shown in FIGS. 2 and 3(a), made up of the mount flange 21, the contact wall 22, the shoulder 23, the straight wall 24, the rounded corner 25, and the bottom 26. The mount flange 21 is, as can be seen in FIG. 1, staked in an annular groove formed on an end wall of the housing 10 to mount the inner cover 2 on the housing 10. The straight wall 24, the shoulder 23, and the contact wall 22 forms the above described side wall 269 of the inner cover 2.

The straight wall 24 has a constant diameter. The shoulder 25 has a diameter increasing toward the contact wall 22. The contact wall 22 has an outer diameter substantially identical with an inner diameter of the outer cover 3 and is contact with the inner wall of the outer cover 3. Numeral 232 in FIG. 3(a) indicates an end perimeter of the contact wall 22 leading to the shoulder 23.

The outer cover 3 is, as clearly shown in FIGS. 2 and 3(a), made up of the mount flange 31, the straight wall 34, the rounded corner 35, and the bottom 36. The mount flange 31 is, like the mount flange 21 of the inner cover 2, staked in the annular groove formed on the end wall of the housing 10 to mount the outer cover 3 on the housing 10 together with the inner cover 2. The straight wall 34 has a constant diameter and forms the side wall 369.

The straight walls 24 and 34 have formed therein the gas inlets 241, 242, 341, and 342, respectively. The gas inlets 241 of the inner cover 2 are the closest to the housing 10. The gas inlets 342 of the outer cover 3 are the farthest from the housing 10. The gas inlets 341 of the outer cover 3 are closer to the housing 10 than the gas inlets 242 of the inner cover 2.

The gas inlets 241 are implemented by six holes (only two are shown in FIG. 2 for the brevity of illustration) which are formed at regular intervals in the peripheral wall of the inner cover 2 and located at the same distance from the end (i.e., the mount flange 21) of the inner cover 2. The same is true for the gas inlets 242, 341, and 342. The gas inlets 241 of the inner cover 2 do not face the gas inlets 341 of the outer cover 3. Similarly, the gas inlets 242 of the inner cover 2 do not face the gas inlets 342 of the outer cover 3.

The distance D1, as shown in FIG. 3(a), between an inner surface 344 of the bottom 36 of the outer cover 3 and an end perimeter 231 of the shoulder 23 of the inner cover 2 leading to the straight wall 24 is preferably within a range of 1.5 mm to 15 mm (10 mm in this embodiment). The distance D2 between an end of each of the gas inlets 241 of the inner cover 2, as viewed in the drawing, close to the housing 10 and the end perimeter 231 of the shoulder 23 of the inner cover 2 is preferably within a range of 0.2 mm to 2 mm (1 mm in this embodiment). The distance C between the inner surface of the outer cover 3 and the outer surface of the inner cover 2 (i.e., the thickness of the clearance 111) is set to 0.5 mm in this embodiment.

Referring back to FIG. 1, the air cover 12 is, as described above, fitted on the boss of the housing 10. The outer cover 121 is provided around the air cover 12 and staked or crimped to retain the water-repellent filter 120 on the periphery of the air cover 12. An elastic insulating holder 14 is fitted in an end of the air cover 12 to hold therein a plurality of leads 15 connected electrically to the gas sensor element 4.

The gas sensor element 4 consists of a cup-shaped solid electrolyte body. The gas sensor element 4 has the outer electrode 41 and an inner electrode (not shown) formed on outer and inner wall thereof, respectively. The gas sensor element 4 has formed therein a cavity into which a ceramic heater 45 is inserted and which defines a reference gas chamber into which the air is introduced as a reference gas through the water-repellent filter 120. The outer electrode 41 is electrically connected to the lead 15 through a lead 43, a terminal 46, and a connector 47. Similarly, the inner electrode is electrically connected to the lead 15 through a terminal 46 and a connector 47. All the leads 15 are connected to a control circuit (not shown) which works to pick up an output of the gas sensor element 4 to determine the concentration of oxygen (also referred to as a measurement gas below) contained in the exhaust gasses admitted into the gas chamber 112 of the cover assembly 11.

The ceramic heater 45 has installed therein a heating element coupled with the leads 15 through terminals 451 and connectors 452. The ceramic heater 45 is supplied with power through the leads 15 and works to heat the gas sensor element 4 up to a desired activation temperature.

The connectors 47 and 452 are disposed in the porcelain insulator 13 installed in the air cover 12.

The operation of the gas sensor 1 of this embodiment will be described below.

The cover assembly 11 has, as described already, the clearance 111 defined between the inner and outer covers 2 and 3 within a specified range. This causes the flow velocity of the measurement gas to be different greatly between the clearance 111 and the inside of the inner cover 2, thus resulting in an increased pressure within the clearance 111, thereby facilitating entrance of the measurement gas into the inner cover 2. A change in concentration of measurement gas occurring outside the gas sensor 1 is, therefore, transmitted quickly into the inner cover 2, thereby providing for a quick response rate of the gas sensor 1.

The clearance 111 also serves to facilitate evaporation of drops of water which have passed through the clearance 111 and stuck to the inner cover 2 by heat dissipation from the covers 2 and 3, thereby minimizing wetting of the gas sensor element 4.

The shoulder 23 of the inner cover 2 defines a wedge-shaped portion of the clearance 111 which works to reduce an upward flow of the measurement gas, as viewed in FIGS. 1 and 2, to the housing 10, thereby straightening the flow of the measurement gas into the gas inlets 241 and 242 of the inner cover 2, which results in quick entrance of the measurement gas into the gas chamber 112.

The distance D2 between the ends of the gas inlets 241 of the inner cover 2 close to the housing 10 and the end perimeter 231 of the shoulder 23 of the inner cover 2 is, as described above, within a specified range of 0.2 mm to 2 mm. This causes the measurement gas to stay between the shoulder 23 and the gas inlets 241, which functions as a buffer promoting the entrance and exit of the measurement gas into and from the gas chamber 112, thus resulting in an improved response rate of the gas sensor 1. If the distance D2 is less than 0.2 mm, it becomes difficult to machine the gas inlets 241 of the inner cover 2. Conversely, if it is more than 2 mm, it will cause the measurement gas to stay within the clearance 111 for a relatively long time, which results a time delay in the entrance and exit of the measurement gas into and from the gas chamber 112. In a case where the gas inlets 241 are located at different levels in the lengthwise direction of the cover assembly 11, then the distance D2 is defined as an interval between the end of one of the gas inlets 241 closest to the housing 10 and the end perimeter 231 of the shoulder 23 of the inner cover 2.

The distance D1, as shown in FIG. 3(a), between the inner surface 361 of the bottom 36 of the outer cover 3 and the end perimeter 231 of the shoulder 23 of the inner cover 2 leading to the straight wall 24 is, as described above, within a specified range of 1.5 mm to 15 mm. This allows the volume of the outer cover 3 to be minimized, thus minimizing the volume of the clearance 111. This results in a decrease in time required for the measurement gas to pass through the clearance 111 and enter the gas chamber 112. If the distance D1 is less than 1.5 mm, it results in increased difficulty of the measurement gas in entering the gas chamber 112 through the inner cover 2. Conversely, if it is more than 15 mm, it results in a time delay in the entrance and exit of the measurement gas into and from the gas chamber 112.

The gas inlets 241, 242, 341, and 342 of the inner and outer covers 2 and 3 are, as described above, identical in area with each other. The area of the gas inlets 241, 242, 341, and 342 is preferably within a range of 0.2 mm$^2$ to 20 mm$^2$. This results in uniformity of streams of the measurement gas from the clearance 111 into the gas chamber 112 through the gas inlets 241 and 242 of the inner cover 2, thus facilitating the replacement of the measurement gas in the gas chamber 112, which provides for a quick response of the gas sensor 1. If the area of the gas inlets 241, 242, 341, and 342 is less than 0.2 mm$^2$, it results in an increased resistance of a gas flow through each of the gas inlets. If it is more than 20 mm$^2$, it facilitates ease of intrusion of water into the gas chamber 112. The gas sensor element 4, thus, gets wet, thus increasing output errors of the gas sensor 1.

The inner and outer covers 2 and 3 have formed in the bottoms 25 and 35 the circular holes 261 and 361 which work as gas outlets to form flow paths of the measurement gas from the gas inlets 242 and 342 to the outside of the cover assembly 11, thereby facilitating the entrance and exit of the measurement gas into and from the gas chamber 112 and the clearance 111.

The inner and outer covers 2 and 3 have the corners 25 and 35 rounded, thus resulting in an increase in service life of a press used in forming the inner and outer covers 2 an 3, which results in a decrease in manufacturing cost of the gas sensor 1.

The gas inlets 242 of the inner cover 2 face the outer electrode 41 of the gas sensor element 4, thus facilitating hits of streams of the measurement gas on the electrode 41, which increases the response rate of the gas sensor 1.

Figure 5:
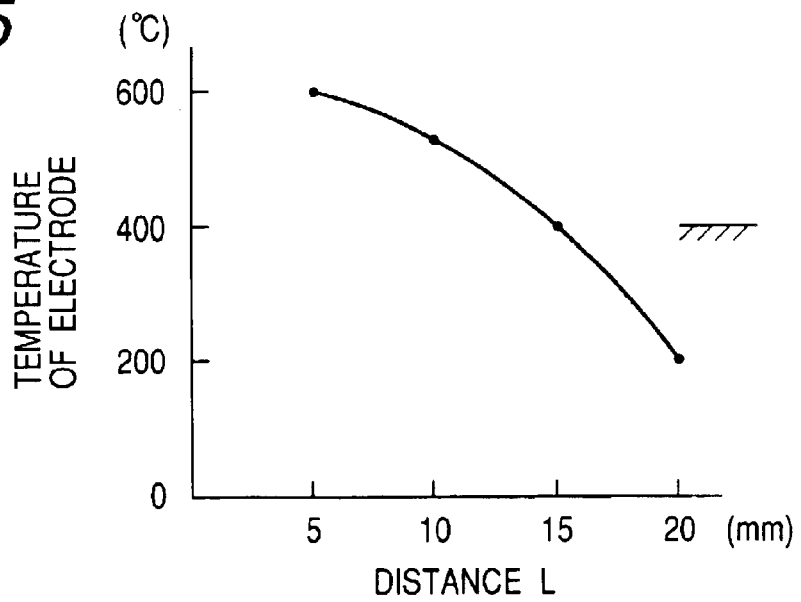
FIG. 5 is a graph which shows the temperature of an outer electrode of a sensor element and the distance of a temperature measurement point from a tip of the sensor element.
Figure 6:
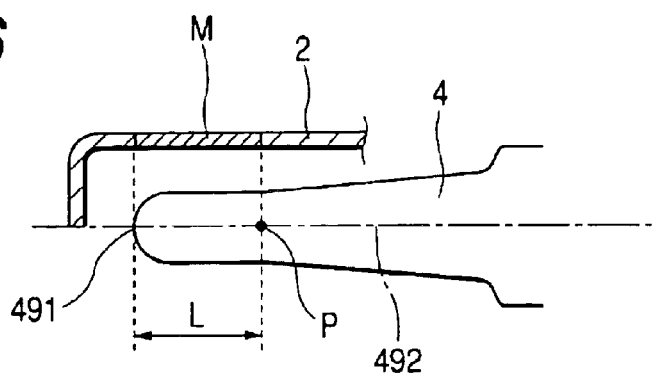
FIG. 6 is an illustration which shows a positional relation between an inner cover of a cover assembly and a head portion of a sensor element.

FIG. 5 is a graph which represents a relation between the temperature of the outer electrode 41 activated by the heating of the heater 45. The heater 45 in this embodiment is installed in the sensor element 4 in direct contact of a head thereof with an inner head surface of the sensor element 4. A head portion of the sensor element 4 is, thus, well heated by the heater 45. U.S. Pat. No. 5,956,841, published Sep. 28, 1999, assigned to the same assignee of this application discloses such a type of gas sensor, disclosure of which is incorporated herein by reference. L indicates the distance between the tip 491 of the sensor element 4, as shown in FIG. 6, and a temperature-measured point P. In FIG. 6, M indicates an area of the inner cover 2 on which the distance L is projected. The broken line 492 indicates a longitudinal center line of the sensor element 4. The graph of FIG. 5 shows that the temperature of the outer electrode 41, as measured at the point P, rises as the distance L increases. It is, thus, preferable that the area M is defined within a desired range of activation temperatures of the outer electrode 41, the gas inlets 241 and 242 are formed within the area M in order to direct the measurement gas to a well-activated portion of the outer electrode 41.

Figure 3B:
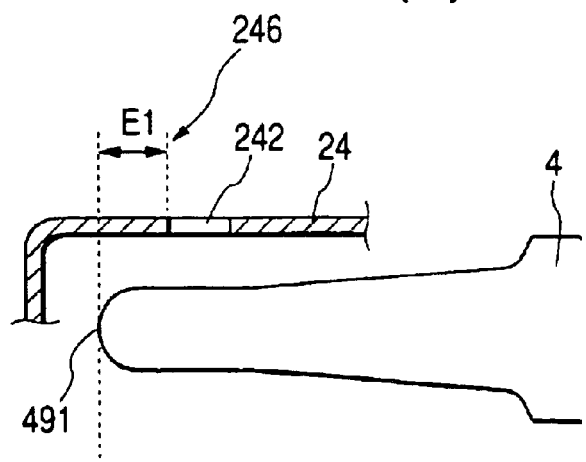
FIG. 3(b) is a partially enlarged view which shows a positional relation between gas inlets and a gas sensor element.

The distance E1, as shown in FIG. 3(b), between the tip 491 of the gas sensor element 4 and ends 246 of the gas inlets 242 of the inner cover 2 close to the tip 491 is preferably within a range of 1.5 mm to 15 mm (4 mm in this embodiment). A portion of the gas sensor element 4 which is opposed to a portion of the heater 45 (i.e., the head of the heater 45 in this embodiment) producing the highest temperature is the most reactive with the measurement gas and contributes to determination of the concentration of the measurement gas greatly. The distance E1 falling within the above range serves to improve the efficiency of hits of streams of the measurement gas on the portion of the gas sensor element 4 that is the highest reactive with the measurement gas.

The distance E2, as shown in FIG. 3(a), between the inner surface 361 of the bottom 36 of the outer cover 3 and ends 343 of the gas inlets 342 which are the closest to the bottom 36 is within a range of 1.5 mm to 15 mm (1.5 mm in this embodiment). As described in FIG. 4, the central stream of the exhaust gas flowing through the flow passage 900 of the exhaust pipe 9 is the highest in flow velocity, while the peripheral stream is the lowest. It is, thus, advisable that the gas inlets 342 of the outer cover 3 be located near the central stream of the exhaust gas for increasing the efficiency of entrance of the measurement gas into the gas chamber 112. The distance E2 within the above range meets this condition in the structure of the gas sensor 1 as illustrated in FIG. 1.

Figure 7:
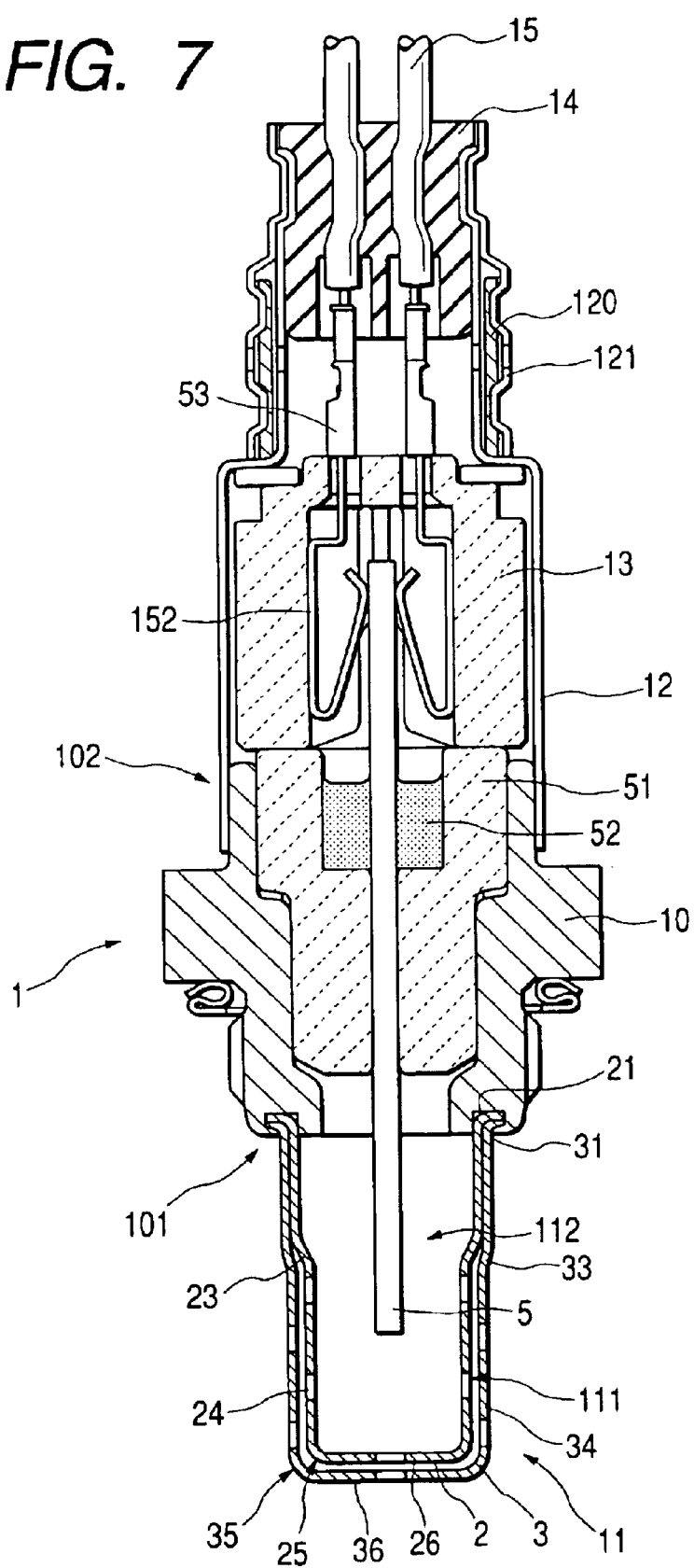
FIG. 7 is a longitudinal sectional view which shows a gas sensor equipped with a protective cover assembly according to the second embodiment of the invention.

FIG. 7 shows the gas sensor 1 according to the second embodiment of the invention which includes the gas sensor element 5 implemented by a laminated plate made up of a base portion and a sensing portion exposed directly to the measurement gas. For example, U.S. Pat. No. 5,573,650, issued on Nov. 12, 1996 to Fukaya et al. teaches a typical laminated sensor element, disclosure of which is incorporated herein by reference.

The gas sensor 1 consists essentially of the metallic hollow cylindrical housing 10, the gas sensor element 5, the air cover 12, the first insulation porcelain 51, the second insulation porcelain 13, and the protective cover assembly 11. The gas sensor element 5 is retained within the housing 10 hermetically. The air cover 12 is fitted on the base portion 102 of the housing 10 to define the air chamber into which the air is, like the first embodiment, admitted through the water-repellent filter 120.

The first insulation porcelain 51 is fitted within the housing 10 and holds therein the gas sensor element 5 in an air-tight fashion using a sealing member 52 made of a glass material, for example. The second insulation porcelain 13 is mounted on the first insulation porcelain 51 in alignment with each other and surrounds the base portion of the gas sensor element 5. The air cover 12 covers the second insulation porcelain 13.

The second insulation porcelain 13 has disposed therein four leads 152 (only two are shown for the simplicity of illustration) each of which is made of a wire folded elastically to make an electric contact at one end with an electrode terminal (not shown) formed on a base end (i.e., an upper end, as viewed in the drawing) of the gas sensor element 5. The leads 152 extend at the other end through holes formed in an end of the second insulation porcelain 13 and connect with the leads 15 through the connectors 53, respectively, for transmission of sensor signals between the gas sensor element 5 and an external control circuit and supply of electric power to a ceramic heater installed in the gas sensor element 5.

The gas sensor element 5 is, as described above, made of the laminated plate which is formed by a sensing section made up of a solid electrolyte layer on which electrodes are formed and insulating layers and the ceramic heater equipped with a heating member.

The cover assembly 11 is, like the first embodiment, made up of the inner and outer covers 2 and 3. The inner cover 2 is identical in structure with the one in the first embodiment, but the outer cover 3 is different from the first embodiment in that a shoulder 33 is formed slightly beneath the shoulder 23 of the inner cover 2, as viewed in the drawing. Other arrangements are identical with those of the first embodiment, and explanation thereof in detail will be omitted here.

Figure 8:
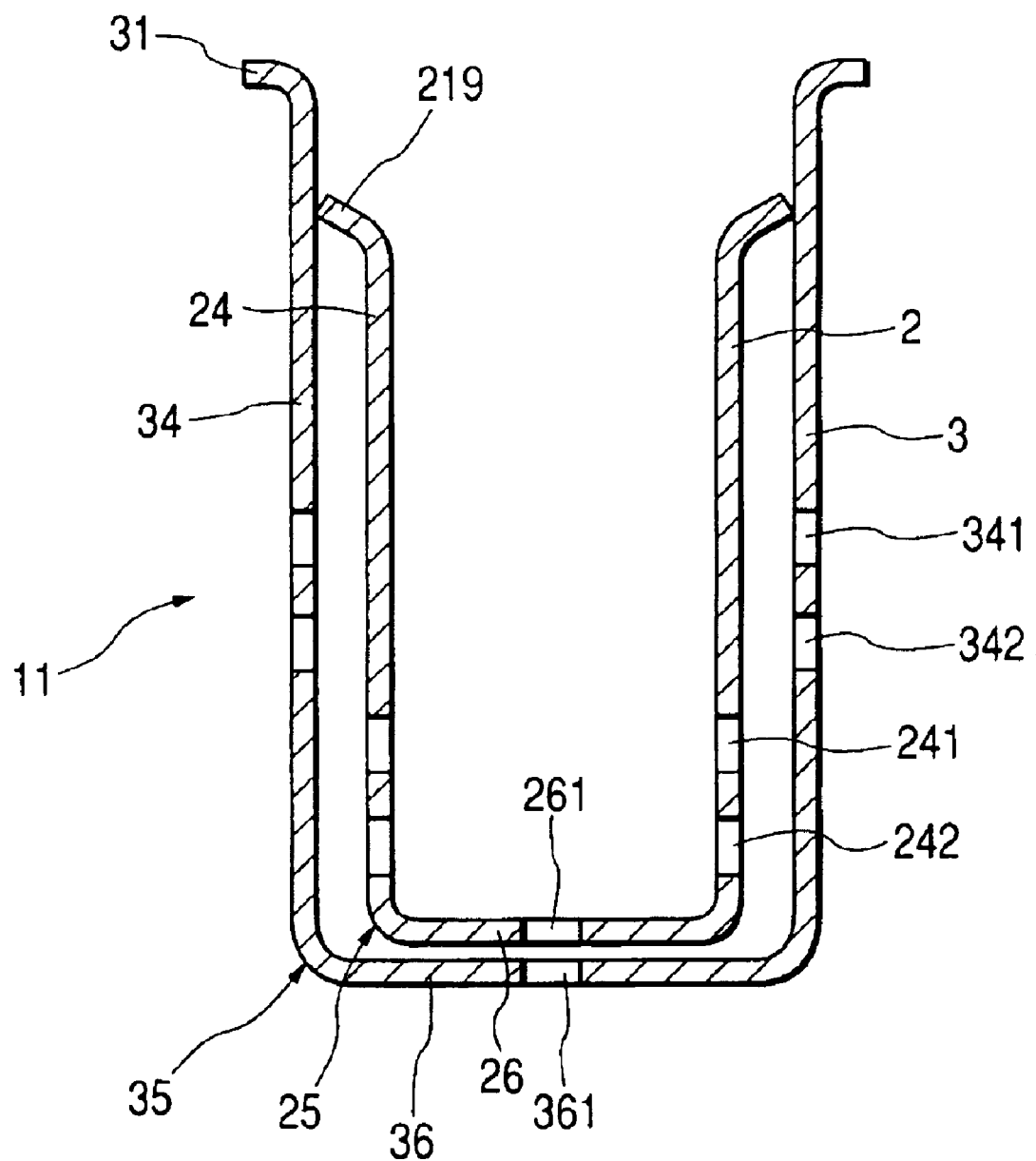
FIG. 8 is a longitudinal sectional view which shows a protective cover assembly according to the third embodiment of the invention.
Figure 9A:
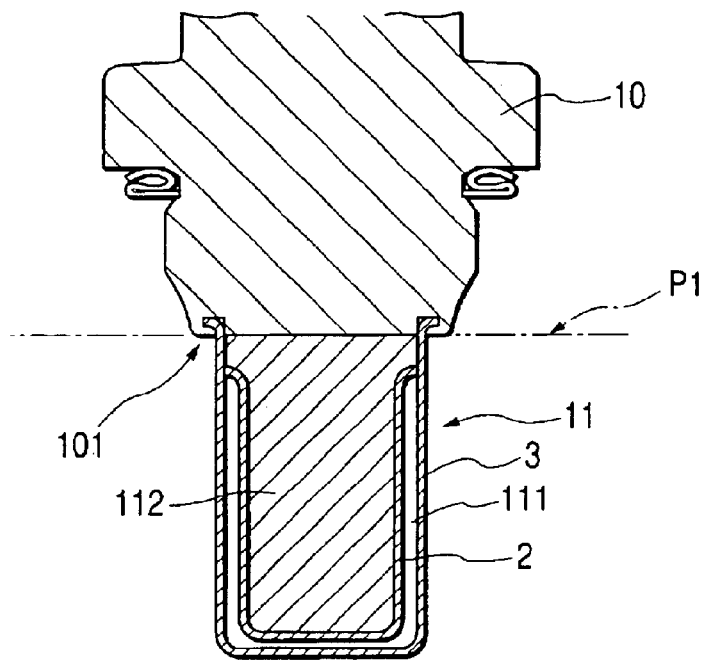
FIG. 9(a) is a partially sectional view which shows a first example of installation of the protective cover assembly of FIG. 8 to a housing of a gas sensor.
Figure 9B:
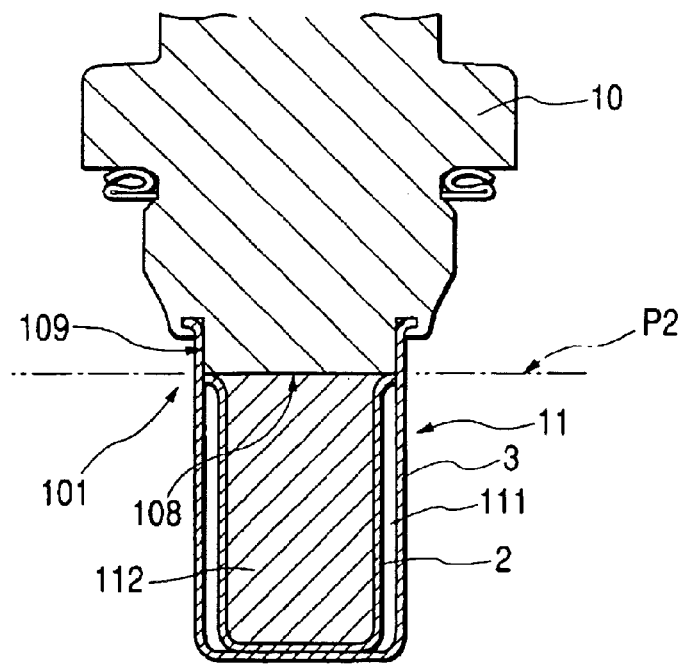
FIG. 9(b) is a partially sectional view which shows a second example of installation of the protective cover assembly of FIG. 8 to a housing of a gas sensor.

FIGS. 8, 9(a), and 9(b) show the protective cover assembly 11 according to the third embodiment of the invention.

The cover assembly 11 is, like the above embodiments, made up of the inner and outer covers 2 and 3 which are formed by straight side walls 24 and 34, respectively.

The inner cover 2 also includes the mount flange 219, the rounded corner 25, and the bottom 26. The gas inlets 242 are formed in the side wall 24 slightly above the rounded corner 25.

The outer cover 3 also includes the mount flange 31, the rounded corner 35, and the bottom 36. The gas inlets 341 and 342 are formed in the side wall 34 and shifted from the gas inlets 241 and 242 of the inner cover 2 toward the mount flange 31. Specifically, the gas inlets 341 and 342 are in misalignment with the gas inlets 241 and 242 in a radius direction of the cover assembly 11. The gas inlets 241, 242, 341, and 342 are identical in size and shape with each other.

The installation of the cover assembly 11 may be achieved in a manner, as illustrated either in FIGS. 9(a) or 9(b).

In FIG. 9(a), the mount flange 31 of the outer cover 3 is staked in an annular groove formed in the end wall 101 of the housing 10. The mount flange 219 of the inner cover 2 is affixed to an inner wall of the outer cover 3.

In FIG. 9(b), the housing 10 has a boss 109. The outer cover 3 is put on the boss 109 and installed at the mount flange 31 in the same manner as in FIG. 9(a). The inner cover 2 is secured on the end surface 108 of the boss 109.

In the case where the cover assembly 111 is installed on the housing 10 in the manner as illustrated in FIG. 9(a), the volume V1 of the inside of the cover assembly 11 (i.e. the gas chamber 112), as indicated by a hatched area in the drawing, defined by the inner cover 2 and the front end of the housing 10 is 846 mm$^3$. The broken line P1 indicates a plane extending over the front surface of the housing 10.

In the case where the cover assembly 11 is installed on the housing in the manner as illustrated in FIG. 9(b), the volume V1 of the inside of the cover assembly 11, as indicated by a hatched area, is 808 mm$^3$. In this case, the volume V1 is equivalent to the volume of the inner cover 2. The broken line P2 indicates a plane extending over the front surface (i.e., the end surface 108) of the housing 10.

The structure of the cover assembly 11, as illustrated either in FIGS. 9(a) or 9(b), results in an increased velocity of flow of the measurement gas in the lengthwise direction of the cover assembly 11 (i.e., the longitudinal direction in the drawing), thus improving the response rate of the gas sensor 1.

The volume V1 may lie within a range of 800 mm$^3$ to 1600 mm$^3$, which results in a decrease in amount of water entering the inner cover 2 to avoid wetting of the gas sensor element 5. If the volume V1 is more than 1600 mm$^3$, it will result in a decrease in ability to replace or freshen the measurement gas in the gas chamber 112.

If the volume of the clearance 111 between the inner and outer covers 2 and 3 is defined as V2, it preferably meets a condition of $V2/V1 \leq 0.25$. This range provides two effects: one is to improve the response rate of the A/F sensor 30 resulting from a difference in flow velocity between the clearance 111 and the inside of the inner cover 2 increased by minimizing the volume V2 of the clearance 111 and the other is to avoid wetting of the sensor element resulting from maximizing of the volume V1 of the gas chamber 112. Note that a lower limit of V2/V1 is more than zero (0) since the volume V2 of the clearance >0.

Other arrangements are identical with those in the first embodiment, and explanation thereof in detail will be omitted here.

Figure 10:
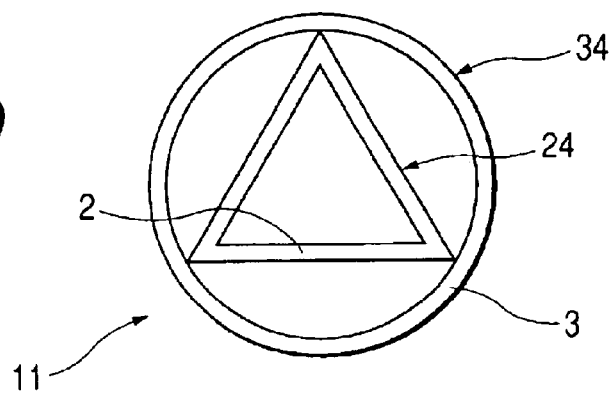
FIG. 10 is a transverse sectional view which shows a protective cover assembly according to the fourth embodiment of the invention.

FIG. 10 shows the protective cover assembly 11 according to the fourth embodiment of the invention.

The outer cover 3 is, like the above embodiments, circular in cross section, while the inner cover 2 is triangular in cross section.

If a circle having the same sectional area as that of the outer cover 3 is defined as S1, and a circle having the same sectional area of the inner cover 2 is defined as S2, the inner and outer covers 2 and 3 are so designed that a difference in radius between the circles S1 and S2 may be within a range of 0.2 mm to 0.6 mm, and preferably within a range of 0.2 mm to 0.55 mm (0.4 mm in this embodiment). The structure of the cover assembly 11 of this embodiment serves to facilitate evaporation of drops of water which have passed through the clearance 111 and stuck to the inner cover 2 by heat dissipation from the covers 2 and 3, thereby minimizing wetting of the gas sensor element 4. If the difference in radius between the circles S1 and S2 is less than 0.2 mm, it is difficult to machine the inner and outer covers 2 and 3 with required dimensional accuracy. Alternatively, if it is more than 0.6 mm, it results in reduction in ability of the cover assembly 11 to replace or freshen the measurement gas in the gas chamber 112.

Other arrangements are identical with those in the first embodiment, and explanation thereof in detail will be omitted here.

Figure 11A:
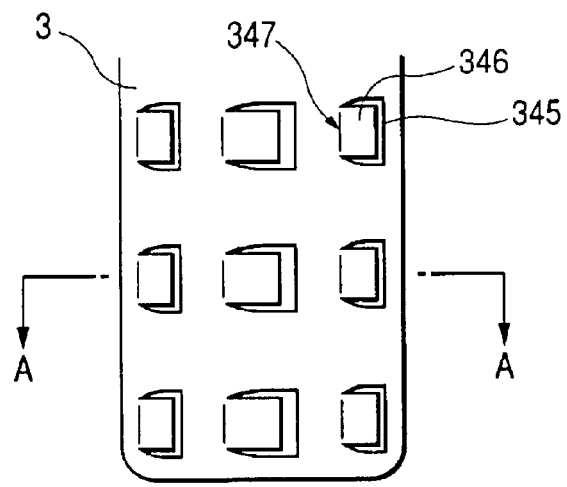
FIG. 11(a) is a partially side view which shows an outer cover of a protective cover assembly according to the fifth embodiment of the invention.
Figure 11B:
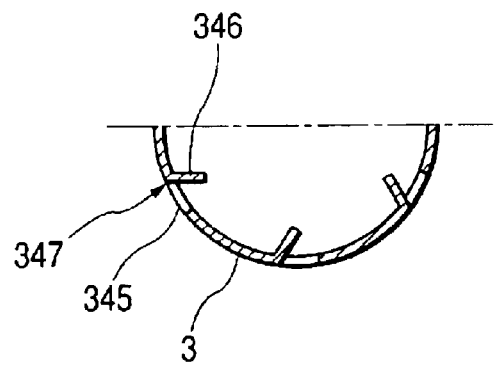
FIG. 11(b) is a partially transverse view, as taken along the line A—A in FIG. 11(a)

FIGS. 11(a) and 11(b) show the outer cover 3 of the protective cover assembly 11 according to the fifth embodiment of the invention. The inner cover 2 is identical in structure with the one in the first embodiment.

The outer cover 3 has formed in a side wall thereof a plurality of gas inlets 345 each of which is formed by cutting a portion of the side wall to a square tab 346 and bending it at a non-cut side 347 thereof inwardly. All the square tabs 346, as clearly shown in FIG. 11(a), have the non-cut side 347 on the same side.

The square tabs 346 projecting inwardly of the outer cover 3 work to form a plurality of streams of the measurement gas in the same direction, thus facilitating ease of entrance of the measurement gas into the outer cover 3.

Figure 12A:
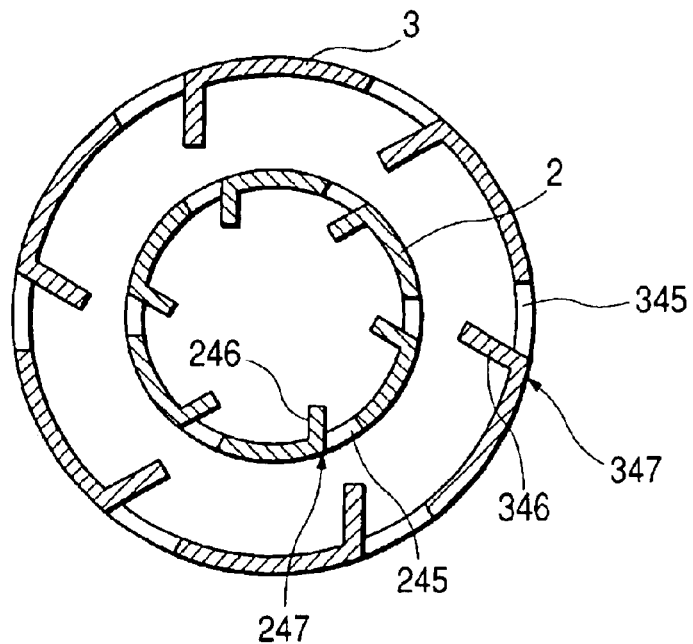
FIG. 12(a) is a transverse sectional view which shows a first modification of a protective cover assembly in the fifth embodiment.
Figure 12B:
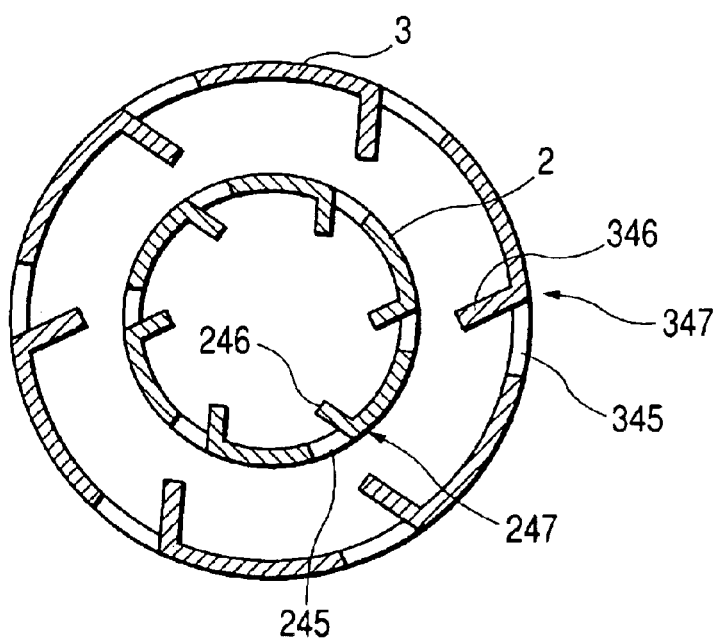
FIG. 12(b) is a transverse sectional view which shows a second modification of a protective cover assembly in the fifth embodiment.

The inner cover 2, as illustrated in FIGS. 12(a) and 12(b), may alternatively have formed in a side wall thereof gas inlets 245 which are identical in shape with the gas inlets 345 of the outer cover 3. Each of the gas inlets 245 is formed by cutting a portion of the side wall to a square tab 246 and bending it at a non-cut side 247 thereof inwardly. All the square tabs 246 of the inner cover 2 and the square tabs 346 of the outer cover 3 are preferably oriented either in a counterclockwise direction, as illustrated in FIG. 12(a), or a clockwise direction, as illustrated in FIG. 12(b), for forming streams of the measurement gas in the same direction to facilitate the ease of entrance of the measurement gas into the gas chamber 112.

Instead of the square tabs 246 and 346, circular or polygonal tabs may be used.

Other arrangements are identical with those in the first embodiment, and explanation thereof in detail will be omitted here.

Figure 13:
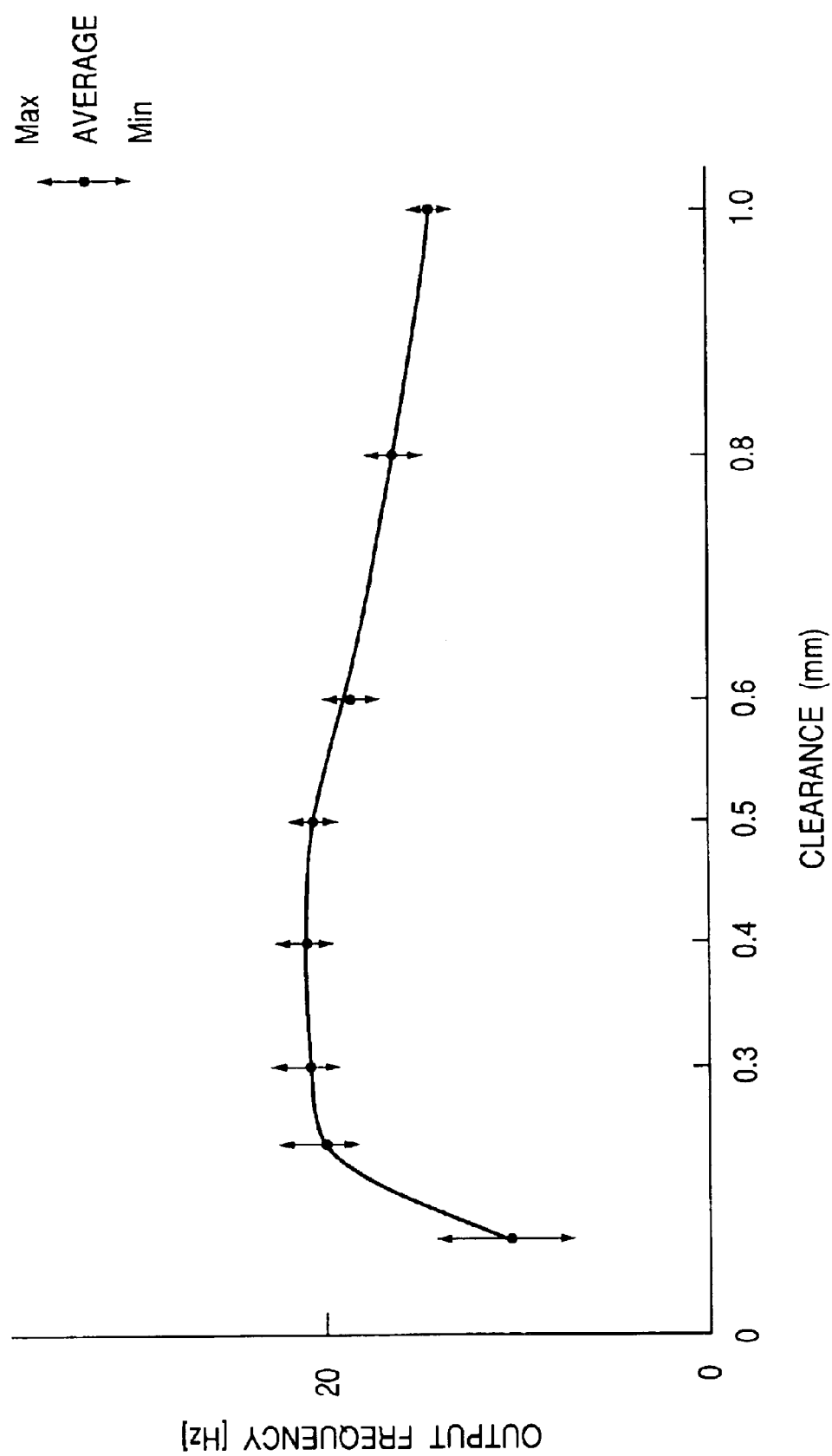
FIG. 13 is a graph which shows a change in frequency of an output of a gas sensor in response to a change in concentration of oxygen for difference values of a clearance between inner and outer covers of a cover assembly.

FIG. 13 is a graph which shows experimental test results indicating a change in frequency of an output of the gas sensor 1 of the first embodiment in response to a change in concentration of oxygen contained in exhaust gasses of the automotive engine for different values of the clearance 111 between the inner and outer covers 2 and 3 of the cover assembly 11. Tests were performed by changing the concentration of oxygen of the exhaust gasses from lean to rich and from rich to lean side sequentially at a time when the output of the gas sensor 1 indicated 0.45V. The texts were made four times for each value of the clearances 111. Maximum, minimum, and average values of outputs of the gas sensor 1 are plotted in the graph.

The graph shows that the frequency of the output of the gas sensor 1 is greatly decreased when the clearance 111 is less than 0.2 mm, and when the clearance 111 is within a range of 0.2 mm to 0.6 mm, it results in an increased velocity at which the exhaust gasses enter and go out of the gas chamber 112, thereby increasing a response rate of the gas sensor 1. If the clearance 111 is more than 0.6 mm, it results in a decreased difference in flow velocity between the inside of the outer cover 3 and the inside of the inner cover 2, thus decreasing the response rate of the gas sensor 1.

Figure 14:
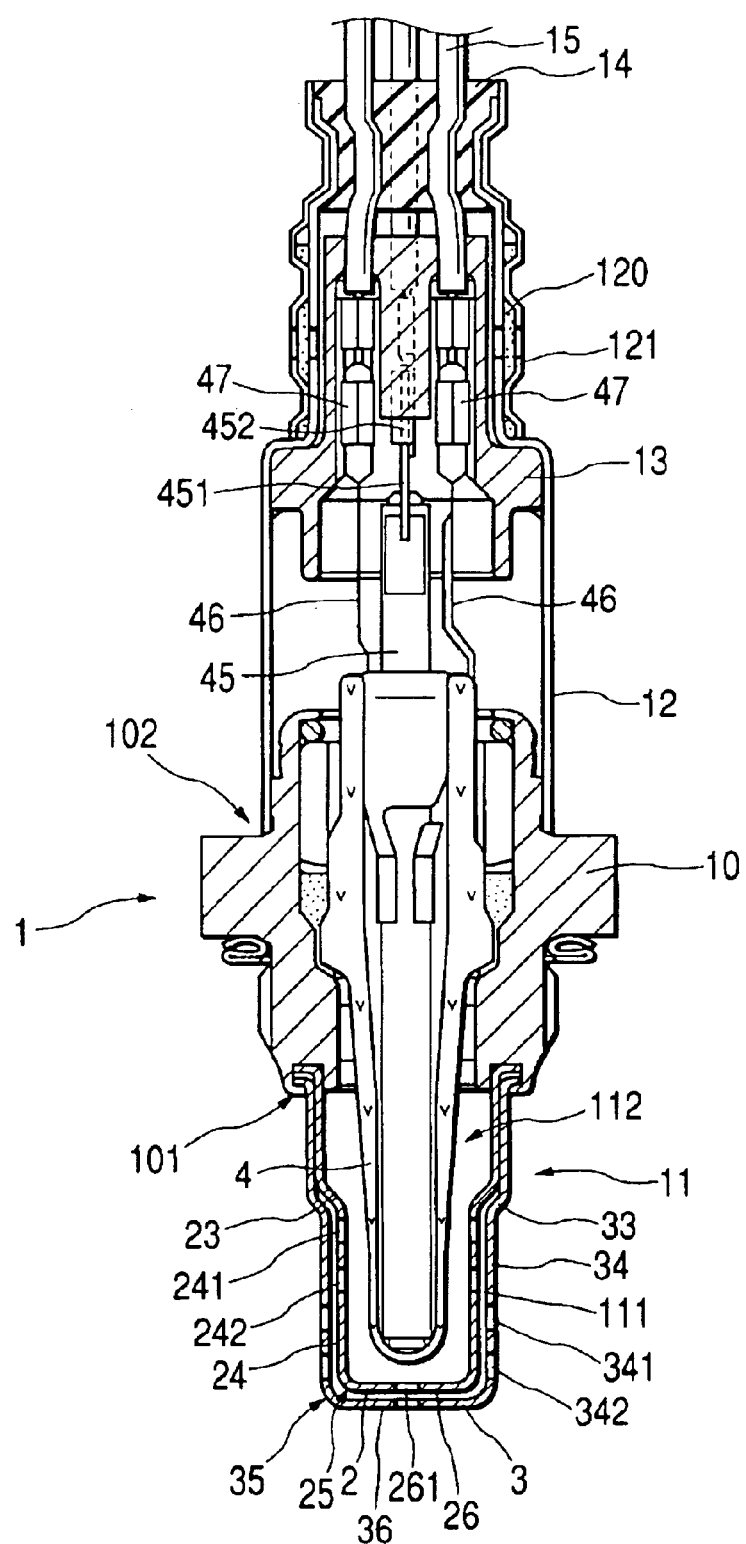
FIG. 14 is a longitudinal sectional view which shows a gas sensor equipped with a protective cover assembly according to the sixth embodiment of the invention.

FIG. 14 shows the gas sensor 1 according to the sixth embodiment of the invention which is a modification of the one shown in FIG. 1.

The inner and outer covers 2 and 3 have the straight walls 24 and 34 and the shoulders 23 and 33, respectively. The gas inlets 241 and 242 of the inner cover 2 are in misalignment with the gas inlets 341 and 342 of the outer cover 3 in the radius direction of the cover assembly 11. The gas inlets 241 and 242 are located closer to the housing 10 than the gas inlets 341 and 342.

The shoulder 23 of the inner cover 2 and the shoulder 33 of the outer cover 3 are substantially flush with each other in the longitudinal direction of the cover assembly 11. Other arrangements are substantially identical with those in the first embodiment, and explanation thereof in detail will be omitted here.

Figure 15:
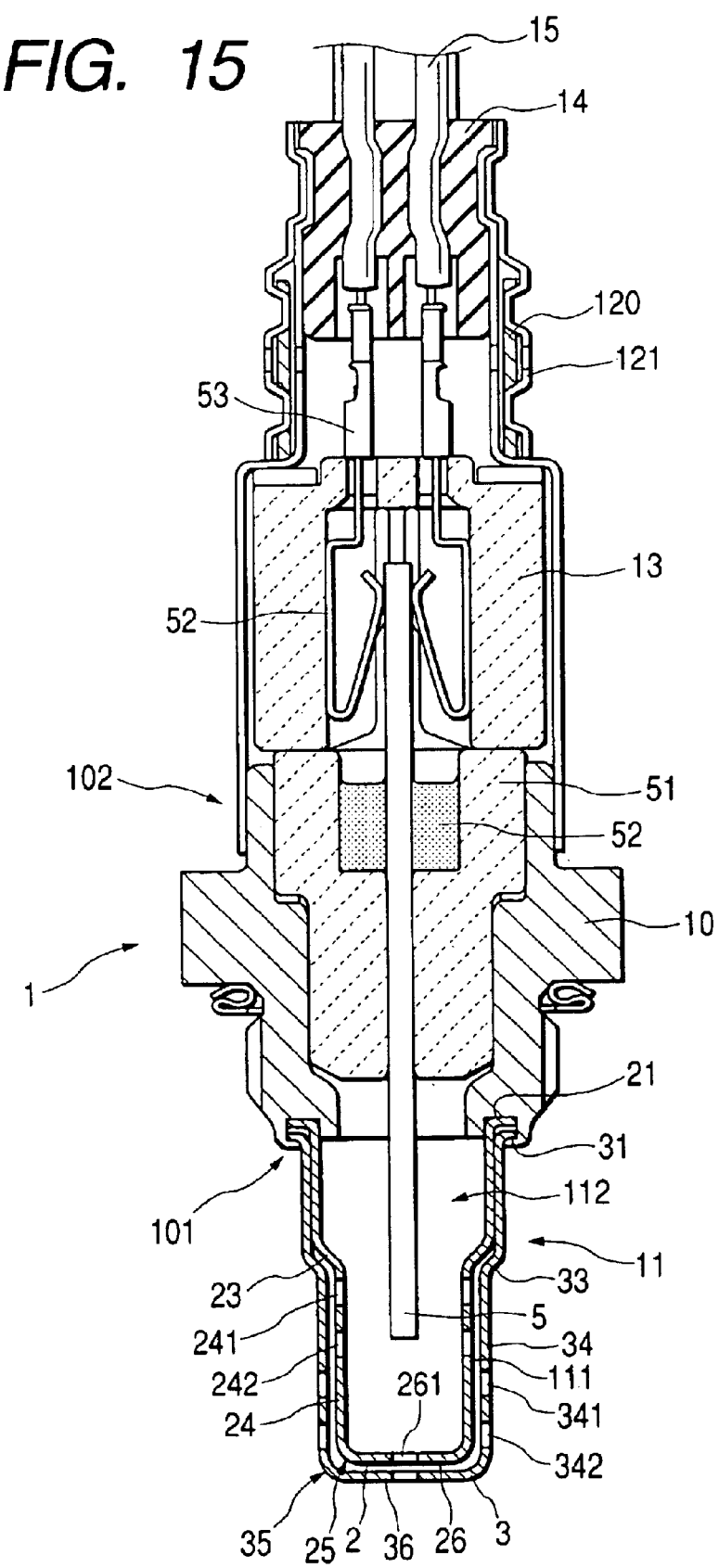
FIG. 15 is a longitudinal sectional view which shows a gas sensor equipped with a protective cover assembly according to the seventh embodiment of the invention.

FIG. 15 shows the gas sensor 1 according to the seventh embodiment in which the cover assembly 11 identical in structure with the one in FIG. 14 is installed on the gas sensor 1, as illustrated in FIG. 7, equipped with the laminated sensor element 5. Other arrangements are identical with those in FIG. 7, and explanation thereof in detail will be omitted here.

The structure of the cover assembly 11 of each of the gas sensors 1 in FIGS. 14 and 15 works to provide two different flow paths A and B. The flow path A forms a flow of the measurement gas which is directed from one of the gas inlets 341 and 342 of the outer cover 3 to another of the gas inlets 341 and 342 through the clearance 111. The flow path B forms a flow of the measurement gas which rises from one of the gas inlets 341 and 342 of the outer cover 3 while circulating through the clearance 111, enters one of the gas inlets 241 and 242 of the inner cover 2, and goes out of the gas outlets 261. The gas flow along the flow path A serves to discharge drops of water heaver than the measurement gas out of the outer cover 3, thereby minimizing the wetting of the gas sensor element.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
   a hollow cylindrical housing;
   a gas sensor element retained within said housing which has a sensing portion working to sense a specified gas; and
   a cover assembly installed on an end of said housing to define a gas chamber in which the sensing portion of said sensing element is disposed and into which the specified gas is admitted, said cover assembly being made up of an inner and an outer hollow cylindrical cover which are different in diameter and have gas inlets through which the specified gas passes, the inner cover being disposed within the outer cover coaxially with each other in a lengthwise direction of the gas sensor with a given clearance therebetween which lies within a range of 0.2 mm to 0.6 mm, the inner cover having a straight wall, extending in parallel to the axis of the inner cover, the gas inlets of the outer cover facing the straight wall of the inner cover and being shifted in a lengthwise direction of the gas sensor from the gas inlets of the inner cover, wherein the gas inlets of each of the inner and outer covers are arrayed along a plurality of lines extending in a longitudinal direction of the inner and outer covers, respectively, and wherein two or more gas inlets are arrayed in each said line.

2. A gas sensor as set forth in claim 1, wherein each of the gas inlets of the inner and outer covers of said cover assembly has an area within a range of 0.2 $mm^2$ to 20 $mm^2$.

3. A gas sensor as set forth in claim 1, wherein each of the inner and outer covers has a bottom in which a hole is formed.

4. A gas sensor as set forth in claim 1, wherein each of the inner and outer covers has a bottom and a rounded corner formed between the bottom and a side wall thereof.

5. A gas sensor as set forth in claim 1, wherein the sensor element has an electrode, and wherein the gas inlet of the inner cover of said cover assembly faces the electrode.

6. A gas sensor as set forth in claim 1, wherein a distance between a tip of the sensing portion of the sensor element remote from said housing and the gas inlet of the inner cover of said cover assembly is within a range of 1.5 mm to 15 mm.

7. A gas sensor as set forth in claim 1, wherein a distance between an end of the outer cover of said cover assembly remote from said housing and the gas inlet of the outer cover is within a range of 1.5 mm to 15 mm.

8. A gas sensor as set forth in claim 1, wherein the clearance between the inner and outer covers lies within a range of 0.2 mm to 0.55 mm.

9. A gas sensor comprising:
a hollow cylindrical housing;
a gas sensor element retained within said housing which has a sensing portion working to sense a specified gas: and
a cover assembly installed on an end of said housing to define a gas chamber in which the sensing portion of said sensing element is disposed and into which the specified gas is admitted, said cover assembly being made up of an inner and an outer hollow cylindrical cover which are different in diameter and have gas inlets through which the specified gas passes, the inner cover being disposed within the outer cover coaxially with each other in a lengthwise direction of the gas sensor with a given clearance therebetween which lies within a range of 0.2 mm to 0.6 mm, the inner cover having a straight wall, extending in parallel to the axis of the inner cover, the gas inlets of the outer cover facing the straight wall of the inner cover and being shifted in a lengthwise direction of the gas sensor from the gas inlets of the inner cover, wherein the gas inlets of the inner and outer covers are of circular shape and identical in area with each other.

10. A gas sensor as set forth in claim 2, wherein the area of each of the gas inlets of the inner and outer covers is 3.14 $mm^2$.

11. A gas sensor comprising:
a hollow cylindrical housing;
a gas sensor element retained within said housing which has a sensing portion working to sense a specified gas; and
a cover assembly installed on an end of said housing to define a gas chamber in which the sensing portion of said sensing element is disposed and into which the specified gas is admitted, said cover assembly being made up of an inner and an outer hollow cylindrical cover which are different in diameter and have gas inlets through which the specified gas passes, the inner cover being disposed within the outer cover coaxially with each other in a lengthwise direction of the gas sensor with a given clearance therebetween which lies within a range of 0.2 mm to 0.6 mm, the inner cover having a straight wall, extending in parallel to the axis of the inner cover, the gas inlets of the outer cover facing the straight wall of the inner cover and being shifted in a lengthwise direction of the gas sensor from the gas inlets of the inner cover, wherein the gas inlets of the inner cover are all in opposed facing relation to an outer electrode of the gas sensor element.

12. A gas sensor as set forth in claim 1, wherein the inner cover further comprises a contact wall, and a shoulder wall extending between said straight wall and said contact wall, the shoulder wall having a diameter increasing toward the contact wall and the contact wall has an outer diameter substantially identical to an inner diameter of said outer cover and is in contact with the inner wall of the outer cover.

13. A gas sensor as set forth in claim 12, wherein a distance between an inner surface of a bottom of the outer cover and a junction of the shoulder wall and the straight wall of the inner cover is within a range of 1.5 mm to 15 mm.

14. A gas sensor as set forth in claim 13, wherein said distance between the bottom of the outer cover and the junction is 10 mm.

15. A gas sensor as set forth in claim 12, wherein a distance between an end of each of the gas inlets of the inner cover closest to the housing and said junction is in a range of 0.2 mm to 2 mm.

16. A gas sensor as set forth in claim 1, wherein a bottom edge end of one of the gas inlets of the outer cover, located closest to a bottom wall of the outer cover, is located closer to said housing than a bottom wall of the inner cover.

* * * * *